United States Patent
Vincek et al.

(10) Patent No.: US 7,138,226 B2
(45) Date of Patent: Nov. 21, 2006

(54) PRESERVATION OF RNA AND MORPHOLOGY IN CELLS AND TISSUES

(75) Inventors: Vladimir Vincek, Aventura, FL (US); Mehdi Nassiri, Miami, FL (US); Mehrdad Nadji, Miami, FL (US); Azorides R. Morales, Coral Gables, FL (US)

(73) Assignee: The University of Miami, Miami, FL (US)

( * ) Notice: Subject to any disclaimer, the term of this patent is extended or adjusted under 35 U.S.C. 154(b) by 453 days.

(21) Appl. No.: 10/141,780

(22) Filed: May 10, 2002

(65) Prior Publication Data

US 2003/0211452 A1 Nov. 13, 2003

(51) Int. Cl.
*C12N 5/00* (2006.01)
(52) U.S. Cl. .................. 435/1.1; 435/374; 436/18
(58) Field of Classification Search .............. 435/1.1, 435/374; 436/18
See application file for complete search history.

(56) References Cited

U.S. PATENT DOCUMENTS

| | | | |
|---|---|---|---|
| 3,389,052 A | 6/1968 | Ehrenreich |
| 3,546,334 A | 12/1970 | Lerner |
| 3,961,097 A | 6/1976 | Gravlee |
| 4,578,282 A | 3/1986 | Harrison |
| 4,656,047 A | 4/1987 | Kok et al. |
| 4,857,300 A | 8/1989 | Maksem |
| 5,104,640 A | 4/1992 | Stokes |
| 5,256,571 A | 10/1993 | Hurley et al. |
| 5,432,056 A | 7/1995 | Hartman et al. |
| 5,460,797 A | 10/1995 | Ryan |
| 5,544,650 A | 8/1996 | Boon et al. |
| 5,679,333 A | 10/1997 | Dunphy |
| 5,849,517 A | 12/1998 | Ryan |
| 5,939,278 A | 8/1999 | Boon et al. |
| 5,976,829 A | 11/1999 | Birnboim |
| 6,017,725 A | 1/2000 | Hoffmann et al. |
| 6,165,723 A | 12/2000 | Shah et al. |
| 6,204,375 B1 | 3/2001 | Lader |
| 6,207,408 B1 | 3/2001 | Essenfeld et al. |
| 6,329,645 B1 | 12/2001 | Giberson et al. |
| 6,379,921 B1 | 4/2002 | Pajak |
| 6,531,317 B1 | 3/2003 | Guirguis et al. |
| 6,586,713 B1 | 7/2003 | Essenfeld et al. |
| 6,793,890 B1 | 9/2004 | Morales et al. |
| 6,797,928 B1 | 9/2004 | Giberson et al. |
| 2002/0086346 A1 | 7/2002 | Ryan |
| 2002/0177183 A1 | 11/2002 | Giberson et al. |
| 2005/0034972 A1 | 2/2005 | Lautenschlager |
| 2005/0074422 A1 | 4/2005 | Visinoni |

FOREIGN PATENT DOCUMENTS

| | | |
|---|---|---|
| DE | 19928820 A1 | 12/2000 |
| DE | 019928820 A1 * | 12/2000 |
| EP | 0311035 A2 | 4/1989 |
| EP | 0311035 B1 | 4/1989 |
| EP | 0311035 A3 | 1/1990 |
| EP | 0562877 A2 | 9/1993 |
| EP | 0822403 A1 | 2/1998 |
| EP | 1455174 A1 | 9/2004 |
| EP | 1455174 B1 | 12/2004 |
| GB | 1557722 | 12/1979 |
| WO | WO 98/21681 | 5/1998 |
| WO | WO 01/44783 A1 | 6/2001 |
| WO | WO 01/44784 A1 | 6/2001 |

OTHER PUBLICATIONS

Ben-Ezra et al., "Effect of Fixation on the Amplification of Nucleic Acids from Paraffin-Embedded Material by the Polymerase Chain Reaction" J. Histochem. Cytochem. 39(3):351-354 (1991).
Bostwick et al., "Establishment of the Formalin-Free Surgical Pathology Laboratory" Arch. Pathol. Lab Med. 118(3):298-302 (1994).
Dimulescu et al., "Characterization of RNA in Cytologic Samples Preserved in a Methanol-Based Collection Solution" Mol. Diagn. 3(2):67-72 (1998).
Florell et al., "Preservation of RNA for Functional Genomic Studies: A Multidisciplinary Tumor Bank Protocol" Mod. Pathol. 14(2):116-128 (2001).
Foss et al., "Effects of Fixative and Fixation Time on the Extraction and Polymerase Chain Reaction Amplification of RNA from Paraffin-Embedded Tissue" Diagn. Mol. Pathol. 3(3):148-155 (1994).
Frable, "Cytology Automation—Focus on Quality Assurance" Am. J. Clin. Pathol. 101(2):121-122 (1994).
Gillespie et al. "Evaluation of Non-Formalin Tissue Fixation for Molecular Profiling Studies" Am. J. Pathol. 160(2):449-457 (2002).
Goldsworthy et al., "Effects of Fixation on RNA Extraction and Amplification from Laser Capture Microdissected Tissue" Mol. Carcinog. 25(2):86-91 (1999).
Hutchinson et al., "Homogeneous Sampling Accounts for the Increased Diagnostic Accuracy Using the ThinPrep Processor" Am. J. Clin. Pathol. 101(2):215-219 (1994).
Koopmans et al., "Optimization of Extraction and PCR Amplification of RNA Extracts from Paraffin-Embedded Tissue in Different Fixatives" J. Virol. Meth. 43(2):189-204 (1993).

(Continued)

*Primary Examiner*—Leon B. Lankford, Jr.
(74) *Attorney, Agent, or Firm*—Nixon & Vanderhye P.C.

(57) ABSTRACT

A solution for preservation and/or storage of a cell or tissue is described. This simple nonaqueous composition can have 10% polyethylene glycol and 90% methanol. It can be used at room temperature. Special chemicals, equipment, and techniques are not needed. Tissue preserved with and/or stored in the solution can be processed for cytology or histology, including chemical staining and/or antibody binding, by a variety of methods; antigen, DNA, and RNA can be extracted from processed tissue in high yield and with minimal or no degradation. Advantages of the solution include: economy and safety, easy access to archival material, and compatibility with both cellular and genetic analyses. The use and manufacture of the solution are also described.

20 Claims, 2 Drawing Sheets

OTHER PUBLICATIONS

Maxwell et al., "Use of Alcohol Fixed Cytospins Protected by 10% Polyethylene Glycol in Immunocytology External" J. Clin. Pathol. 52(2):141-144 (1999).

Morales et al. "Continuous-Specimen-Flow, High-Throughput, 1-Hour Tissue Processing" Arch. Pathol. Lab Med. 126(5):583-590 (2002).

Sato et al., "A Simplified Technique of Tissue Processing and Paraffin Embedding With Improved Preservation of Antigens for Immunostaining" Am. J. Pathol. 125(1):431-435 (1986).

Sato et al., "The AmeX Method: A Multipurpose Tissue-Processing and Paraffin-Embedding Method. III. Extraction and Purification of RNA and Application to Slot-Blot Hybridization Analysis" J. Pathol. 163(1):81-85 (1991).

Shibutani et al., "Methacarn Fixation: A Novel Tool for Analysis of Gene Expressions in Paraffin-Embedded Tissue Specimens" Lab. Invest. 80(2):199-208 (2000).

Takahashi et al., "Freeze Substitution and Freeze Drying for Stable, Long-Term Preservation of Cytologic Specimens for Immunostaining" Acta Cytol. 40(3):396-400 (1996).

Ambion, "Preserve RNA in the Tissue Before RNA Isolation" (2002) TechNotes 8(2), 3 pages.

Ambion, "RNAlater™ Tissue Collection: RNA Stabilization Solution" (2002) Catalog #7020, 5 pages.

Ambion, "Paraffin Block RNA Isolation™" (2002) Catalog #1902, 6 pages.

Qiagen, "Rneasy® Protect and RNAlater™ Handbook" (Aug. 2000) pp. 1-27.

Qiagen, "Rneasy Midi/Maxi Protocol for Isolation of Total RNA from Animal Tissues" (Jun. 2001) Rneasy Midi/Maxi Handbook, pp. 41-47.

Cytyc, "PreservCyt® Solution" (2001) Catalog #0234004, 1 page.

Cytyc, MSRP for PreservCyt® Solution (Oct. 2001), 4 pages.

Woods & Ellis, Laboratory Histopathology (1994) web site: home.primus.com.au/royellis/histo.html.

Leong, "Fixation and Fixatives" from Woods & Ellis, Laboratory Histopathology (Churchill Livingstone, 1994).

Winsor, "Tissue Processing" from Woods & Ellis, Laboratory Histopathology (Churchill Livingstone, 1994).

Gormley et al., "Resin Embedding for Light Microscopy" from Woods & Ellis Laboratory Histopathology (Churchill Livingstone, 1994).

NCI Protocol, "70% Ethanol Fixation" (2002) 1 page.

Boon et al. "Microwave-stimulated diffusion for fast processing of tissue: Reduced dehydrating, clearing, and impregnating times" Histopathol. 10:303-309 (1986).

Boon et al. "Formaldehyde fixation and microwave irradiation" Histochem. J. 20:313-322 (1988).

Boon et al. "Microwave irradiation of human brain tissue: Production of microscopic slides within one day" J. Clin. Path. 41:590-593 (1988).

Kok et al. "Major improvement in microscopic-image quality of cryostat sections" Am. J. Clin. Pathol. 88:620-623 (1987).

Kok et al. "Histoprocessing with the microwave oven: An update" Histochem. J. 20:323-328 (1988).

Kok et al. "Microwaves for microscopy" J. Microscopy 158:291-322 (1990).

Kok et al. "Physics of microwave technology in histochemistry" Histochem. J. 22:381-388 (1990).

Kok et al. "Ultrarapid vacuum-microwave histoprocessing" Histochem. J. 27:411-419 (1995).

Leong et al. "Antigen preservation in microwave-irradiated tissues: A comparison with formaldehyde fixation" J. Pathol. 156:275-282 (1988).

Leong et al. "Microwave fixation and rapid processing in a large throughput histopathology laboratory" Pathol. 23:271-273 (1991).

Lewis et al. "Unlocking the archive—Gene expression in paraffin-embedded tissue" J. Pathol. 195:66-71 (2001).

Morales et al. "Experience with an automated microwave-assisted rapid tissue processing method" Am. J. Clin. Pathol. 121:528-536 (2004).

Rohr et al. "A comparison of routine and rapid microwave tissue processing in a surgical pathology laboratory" Am. J. Clin. Pathol. 115:703-708 (2001).

Suurmeijer et al. "Notes on the application of microwaves in histopathology" Histochem. J. 22:341-346 (1990).

Van Dort et al. "Preservation of structure and cytochemical reactivity at the ultrastructural level, using microwave irradiation" Histochem. J. 20:365-372 (1988).

Vincek et al. "A tissue fixative that protects macromolecules (DNA, RNA, and protein) and histomorphology in clinical samples" Lab. Invest. 83:1427-1435 (2003).

Visinoni et al. "Ultra-rapid microwave/variable pressure-induced histoprocessing: Description of anew tissue processor" J. Histotechnol. 21:219-224 (1998).

Morales "Comparative usefulness of standard and microwave-assisted tissue processing methods" Histologic 35:40-46 (2002).

Morales "Histopathology while-u-wait?" Bull. Royal Coll. Pathol. 128:19-21 (2004).

* cited by examiner

PRESERVATION OF RNA AND MORPHOLOGY IN CELLS AND TISSUES

BACKGROUND OF THE INVENTION

1. Field of the Invention

The present invention relates to a composition containing polyethylene glycol (PEG) and methanol for preservation of a cell or tissue, especially at ambient temperature. It may also be used for cell or tissue storage. A cell or tissue preserved with and/or stored in compositions of the present invention maintains its morphological characteristics, the recognition of its antigens by cognate antibodies, and the integrity of its nucleic acids (e.g., DNA and RNA) without requiring refrigeration or freezing.

2. Description of the Related Art

Cytological and histological processing prevents autolysis of cells and tissue, respectively, after their removal from a living body. Moreover, the structure of individual cells and their organization within the tissue are stabilized by such processing. There is a requirement, however, for sophisticated procedures and dedicated instruments in most cases to process cells and tissues in a clinical setting. Therefore, specimens are usually collected in physician offices or surgical suites, and transported to a centralized pathology service. Suitable compositions for the preservation and/or storage of a cell or tissue are needed to ensure that autolysis is prevented and that cellular morphology, antigen, and nucleic acid are maintained until processing.

Furthermore, genetic analysis is becoming more important by itself or complementary to cell staining, enzyme assays, and immunological techniques in pathology. Expression of mutant genes or the over-expression of normal genes can be examined by analyzing nucleic acid. In situ detection of RNA can localize transcripts within tissue containing different types of cells; this can also be accomplished by detecting RNA that has been extracted from different portions of sorted cells or sectioned tissue. Mutations may be seen in DNA or RNA. Alternating cytologic/histologic and genetic analyses of sorted cells or sectioned tissue can be used to correlate pathological events at cellular and molecular levels. Genetic analysis will be possible only if degradation is prevented and macromolecular structures are stabilized. But many preservative compositions and fixatives cause irreversible damage (e.g., activity of the ubiquitous nuclease enzymes, hydrolysis of phosphodiester bonds, and/or deamidation of bases) to the structure of nucleic acids (e.g., DNA, and especially RNA) and reduce their yield, thereby limiting the usefulness of genetic techniques for diagnosis and research applications. Consequently, preservation of nucleic acids in a fresh cell or tissue usually requires special handling, such as immediate processing or freezing, to allow examination by a combination of cytologic, histologic, immunologic, and genetic techniques.

The composition disclosed herein may be used to advantage in conventional tissue processing or other processing methods such as described in U.S. Pat. No. 6,207,408; WO 01/44783; and WO 01/44784. Conventional techniques are described in general references such as Thompson (*Selected Histochemical and Histopathological Methods*, Springfield, Ill.: Thomas, 1966), Sheehan & Hrapchak (*Theory and Practice of Histotechnology*, St. Louis, Mo.: Mosby, 1973), Bancroft & Stevens (*Theory and Practice of Histological Techniques*, New York, N.Y.: Churchill Livingstone, 1982); Boon & Kok (*Microwave Cookbook of Pathology*, Leiden, NL: Coulomb, 1989); Woods & Ellis (*Laboratory Histopathology*, New York, N.Y.: Churchill Livingstone, 1994). U.S. Pat. Nos. 3,389,052; 3,546,334; 5,104,640; 5,256,571; 5,849,517; and 6,204,375; Florell et al. (Mod. Pathol., 14:116–128, 2001); Bostwick et al. (Arch. Pathol. Lab. Med., 118:298–302, 1994); Dimulescu et al. (Mol. Diagnosis, 3:67–71, 1998); Maxwell et al. (J. Clin. Pathol., 52:141–144, 1999) Shibutani et al. (Lab. Invest., 80:199–208, 2000); and Gillespie et al. (Am. J. Pathol., 160:449–457, 2002) describe preservative and fixative solutions.

Compositions of the present invention are novel and nonobvious. They are nonaqueous solutions comprising PEG and methanol, which preserve morphological characteristics, recognition of antigen by cognate antibody, and integrity of nucleic acid (e.g., DNA and RNA) in an isolated cell or solid tissue without the inconvenience of cooling or freezing the specimen to prevent degradation. Thus, an isolated cell or solid tissue can be stored for long times at ambient temperature. Further advantages of and improvements due to the invention are discussed below.

SUMMARY OF THE INVENTION

It is an object of the invention to provide a composition for cell or tissue preservation and/or storage. The composition contains a polyethylene glycol and methanol. It is conveniently a nonaqueous solution with a melting point that is substantially below the ambient temperature. Cells may be preserved or stored for cytology; tissues may be preserved or stored for histology. Antigen or nucleic acid from the cell or tissue may be analyzed. Preservation of morphology can be assessed with a microscope. Antigen and nucleic acid preservation may be assessed by yield of at least partially nondegraded antigen and nucleic acid after extraction from the cell or tissue, or enhanced antibody binding and complementary probe hybridization to the cell or tissue. Also provided are methods of making and using the composition.

Another object of the invention is a specimen holder containing the composition.

A cell or tissue preserved and/or stored in accordance with the invention may be further processed for cytologic, histologic, immunologic, and/or genetic analysis. The isolated cells may be provided in the form of a pellet, smear, or suspension; a section or block of tissue obtained after impregnation may also be provided. Nucleic acid (e.g., DNA or RNA) extracted from preserved, stored, or processed isolated cells or solid tissue is yet another embodiment of the invention.

Further embodiments of the invention are described in detail below or would be apparent to the skilled artisan from the disclosure herein.

SPECIFIC EMBODIMENTS OF THE INVENTION

Figure 1A:
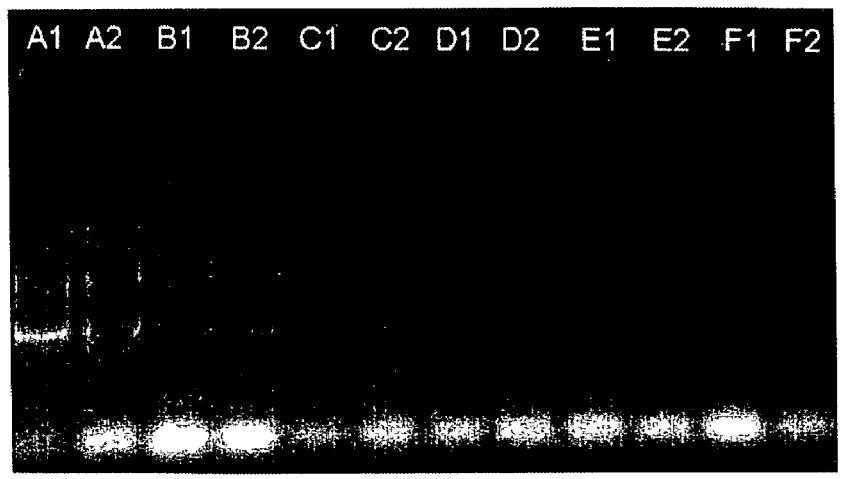
FIG. 1 shows an ethidium bromide stained agarose gel where RNA was been separated under denaturing conditions. After tissue was incubated in different compositions for three days (FIG. 1A) or one week (FIG. 1B) at about 25° C., RNA was extracted using a Trizol RNA Isolation kit (Gibco BRL). Each sample (A to F) was run in duplicate lanes (1 and 2).

Compositions described herein were developed for their chemical simplicity, ability to preserve morphologic and genetic characteristics of tissue, and convenience and practicality of usage at ambient temperature. A cell or tissue may be stored therein and serve as an archival source for cytology, histology, and/or genetic analysis. It may be preserved and/or stored for prospective or retrospective study. Although not preferred, storage in the composition of the present invention may also follow contact of the cell or tissue with other preservatives and/or fixatives.

Cell may be pellets or suspensions, preferably isolated cells from a biological fluid (e.g., ascites, blood, cerebrospinal fluid, lymph, pleural exudate), cell suspensions from the aspiration of organs or lavage of body cavities, or cell smears (e.g., cervix). Cells may be isolated by enzymatic and/or mechanical disaggregation. They may be cultured as live cells for maintenance or propagation before preservation and/or storage. Cells may be washed and collected by centrifugation into a pellet; they may be collected on a slide or other substrate. For blood and other single-cell suspensions, cells may be isolated by sedimentation or density gradient centrifugation, panning on a coated or uncoated plastic plate, passage through glass wool, resetting, sorting by light scatter or fluorescently-labeled antibody, binding to antibody-coated magnetic particles, or a combination thereof. Cells may be cancerous (benign or malignant) or precancerous, obtained from an animal or human subject affected by disease or suspected of same (normal or diseased), or be affected by other pathology. It may be obtained by autopsy or biopsy (e.g., catheterization or phlebotomy) or other fluid collection. Cells should be placed in contact with the composition within one to 30 min after removal from the body or in vitro culture, but this time may be extended by cooling them on ice. It may be preserved and/or stored.

The tissue may be processed as disclosed herein. It is usually a solid tissue such as, for example, parenchyme, connective or fatty tissue, heart or skeletal muscle, kidney, liver, skin, smooth muscle, or spleen. Optionally, calcified tissue may need to be demineralized before further processing. But "tissue" does not usually refer to single cells from a biological fluid (e.g., ascites, blood, pleural exudate), cell suspensions from the aspiration of organs or lavage of body cavities, or cell smears. The tissue may be a tumor (benign or malignant), cancerous or precancerous, obtained from an animal or human subject affected by disease or suspected of same (normal or diseased), or be affected by other pathology. It may be obtained by autopsy or biopsy (e.g., endoscopy or laparoscopy) or surgical resection. Tissue should be placed in contact with the composition within one to 30 min after death or removal from the body but this time may be extended by cooling it on ice. A piece of tissue (e.g., a slice or block) may be preserved with and/or stored in the composition of the invention; tissue that has been preserved and/or stored may also be embedded in a medium.

Cells may be processed for cytology. They may be smeared on a slide and examined with a microscope. Antigen or antibody may be directly or indirectly labeled with a colorimetric, enzymatic, fluorescent, luminescent, magnetic, or radioactive moiety which is detectable. Cells may be identified and/or isolated in accordance with antigen expression by antibody panning or sorting. A cytometer may analyze such cells; a cell sorter may separate cells by size, viability, binding of fluorescent-labeled antibody, or a combination thereof. A magnet may be affinity purify cells that bind an antibody-coated magnetic bead. Negative or positive selection may be used to isolate cell populations.

Conventional histological processing usually involves a fixing agent that cross links reactive biomolecules (e.g., aldehyde-containing aqueous solution like buffered formalin), although sometimes a fixing agent that is a coagulant or precipitant (e.g., a ketone) is used. The tissue specimen is often dehydrated through a graded series of ethanol (e.g., from 70% to 100%) and then cleared in a series of xylenes prior to impregnation. Processing usually occurs over several hours or days (e.g., overnight).

Histological processing in accordance with the method described in U.S. Pat. No. 6,207,408, may be comprised of incubation in a series of nonaqueous solutions under various conditions of time, temperature, and pressure. The tissue may be fixed, dehydrated, optionally cleared, and impregnated; alternatively, the tissue may be hardened and impregnated. The boundaries of each step may overlap because a chemical component of one of the series of solutions has two or more activities (e.g., fixing agent, dehydrating agent, and clearing agent). Tissue processing may be completed in 45 min, one hour or less, 90 min or less, or two hours or less. Rapid and continuous processing is accomplished by decreasing the thickness of tissue specimens, use of a series of nonaqueous solutions composed of admixtures, heating with microwave energy, driving solvent/solute exchange in tissue specimens under pressure or by dilution, mechanical agitation, addition of an enhancer or surfactant, or a combination thereof.

The admixture may include at least one fixing agent, at least one dehydrating agent, and at least one agent that clears tissue and/or removes fat (e.g., chosen from alcohols, ketones, xylenes). Another admixture may include at least one clearing agent and at least one impregnating agent (e.g., xylenes, waxes). The tissue specimen may be impregnated in a wax solution comprised of a mixture of different chain lengths (e.g., mineral oil which is liquid and paraffin which is solid at ambient temperature). It should be noted that although many chemicals have multiple activities, preferred admixtures contain more than one chemical. Preferably, an admixture contains at least two or three different chemicals (e.g., isopropanol, PEG, and acetone; isopropanol, acetone, and paraffin). Tissue specimens may be 3 mm or less in their smallest dimension to allow adequate diffusion: e.g., the thickness of a tissue slice or block may be between 0.5 mm and 2.0 mm thick, preferably 1.5 mm or less, and more preferably 1.0 mm or less. See U.S. Pat. No. 6,207,408.

Embedding medium may be nitrocelluloses, plastics, resins, and waxes. Tissue processing serves to irreversibly inactivate enzymes responsible for autolysis and degradation of biopolymers (e.g., nucleic acids, protein, antigens). Therefore, blocks of embedded tissue or sections thereof may also be stored. Nucleic acids (e.g., DNA or RNA) may by extracted from the tissue or sections, preferably after removal of the embedding medium. A tissue section may be between 3 µm to 6 µm thick (nitrocellulose or wax) or 0.5 µm to one µm thick (plastic or resin).

Studies with tissues preserved in compositions of the present invention indicate better preservation of nucleic acids than with conventional preservative solutions. The fresh tissue is contacted with the composition in accordance with the present invention, and can be processed for cytologic, histologic, immunologic, and/or genetic studies soon after delivery to the laboratory, or archival material may be stored and made available for future research and other applications. Improvements are observed in the yield of genetic material, the stability of the genetic material in archival form, the size and integrity of the genetic material, and reducing chemical modification of the genetic material in comparison to the prior art.

The preservative composition of the present invention comprises polyethylene glycol (PEG) or the like. The PEG preferably has a melting point below ambient temperature. It may have an average molecular weight of about 800 daltons or less, preferably about 600 daltons or less, more preferably about 400 daltons or less, and even more preferably about 300 daltons or less; the average molecular weight may be between 0 to about 800 daltons, between about 100 to about 600 daltons, or between about 200 daltons to about 400 daltons. The term "about" when referring to the average molecular weight of PEG means that a variation of 10, 25 or 50 daltons is permissible. The higher molecular weight PEG (e.g., 1000 average molecular weight or more) are not preferred although they may be present in amounts of less than 5%, 10% or 20% of the molecular weight distribution. The melting point of PEG 400 is about 4° C.–8° C. and PEG 600 is about 20° C.–25° C. The melting point of PEG used in the composition may be 37° C. or less, 32° C. or less, 27° C. or less, 22° C. or less, 15° C., or less, 10° C. or less, or 5° C. or less; the lower melting points are preferred for tissues that are refrigerated or chilled during storage.

The PEG concentration in the present invention may be about 20% (v/v) or less, more preferably about 15% (v/v) or less, about 5% (v/v) or more, about 10% (v/v) or more, and any intermediate range thereof. The term "about" when referring to concentration of PEG means that a variation of 1% (v/v) or 2.5% (v/v) is permissible. PEG has a density of about 1.1 to 1.2 gm/ml depending on its molecular weight so the concentrations given herein may be converted between weight and volume measurements using 1.1 as the specific gravity.

The preservative composition of the present invention also comprises methanol or the like. Alcohols such as, for example, ethanol are not effective to preserve tissue for both morphologic and genetic analyses. But most histotechnologists prefer ethanol over methanol and would not be motivated to substitute between alcohols because of methanol's volatility, flammability, and cost. But in accordance with the teachings of the present invention, methanol is required for effective preservation of tissue. Fixatives which cross link reactive groups (e.g., aldehydes, ketones) are not required.

The methanol concentration in the present invention may be about 95% (v/v) or less, more preferably about 90% (v/v) or less, about 80% (v/v) or more, about 85% (v/v) or more, and any intermediate range thereof. The term "about" when referring to concentration of methanol means that a variation of 2.5% (v/v) or 5(v/v) is permissible. Methanol has a density of about 0.79 gm/ml so the concentrations given herein may be converted between weight and volume measurements using 0.79 as the specific gravity.

Special procedures such as, for example, agitation/shaking, microwaving, ultrasound, heating or cooling from ambient temperature, freezing, or immediate processing are not required for effective preservation in accordance with the present invention. The invention allows preservation and/or storage at ambient temperature (e.g., below 42° C., 37° C., or 30° C.; between 15° C. to 30° C., or 20° C. to 25° C.). Thus low temperatures (e.g., about 4° C. or below 15° C.) are not required for preservation but may be used for storage. For a gram of tissue, about 10 ml to 25 ml of the composition may be used as a preservative and/or storage medium. Tissue may sliced thinly (e.g., about one mm, 1.5 mm, 2 mm, 2.5 mm, 3 mm, 3.5 mm, or 4 mm or less in the slice's smallest dimension) to encourage passage of the composition into the tissue. Storage may be for more than one week, two weeks, one month, three months, six months, or one year.

The composition of the present invention (i.e., a nonaqueous solution at ambient temperature) may be manufactured by mixing PEG and methanol in amounts appropriate to achieve desired concentrations. Minor amounts of other chemicals may be tolerated if they do not affect the composition's ability to act as a preservative. While the composition initially does not contain added water, there may be a minor amount of water present because of the hygroscopic properties of PEG and methanol or later extraction of water from the tissue.

The composition of the present invention may be provided within a tissue holder, which is preferentially adapted to immerse the tissue and avoid spillage. A holder may have a total volume of 30 ml to 50 ml, which is large enough for one or more gram-sized pieces of tissue to be immersed in the composition (e.g., at least 50–90% of the total volume). For example, a glass or plastic vial with an attached or separate closure (e.g., fitted lid or cap) may be used; alternatively, a plastic bag with a sealable portion may require elimination of empty spaces to ensure immersion. Preferred is a screw cap with a gasket to prevent spillage that is threaded on a nonopaque vial. Larger volumes may be provided in a bottle, bucket, or carboy with spigot. The holder may be provided with a container (e.g., hinged cassette, mesh bag, porous sponge) that can be placed therein and which surrounds small pieces of tissue and encourages solution exchange. The holder may be adapted for solid tissue such that pieces thereof are immersed in the composition. Preferentially, the solid tissue is surrounded on all surfaces by reducing air pockets in the holder and/or having a container therein.

Tissue holders may be packaged between a half-dozen to a gross of units (e.g., 25 or 100) in a carton; holder and container may be separately packaged in a single-use kit to collect tissue. It would be convenient to mark each holder with an indivisual identifier (e.g., alphanumeric printing, bar code) or a writeable surface to customize the identifier (e.g., information about source of the tissue or analysis to be performed). Unlike holders for blood or pap smears or single cell suspensions, having a slide or swab contained therein is not preferred because they would be of limited usefulness for solid tissues.

Tissue Processing

Fixation initiates hardening of the tissue specimen, and preserves morphology by stabilizing proteins and halting degradation. Without chemical fixation, endogenous enzymes will catabolize and lyse the cell, and the tissue's morphology will be altered. Indications that fixation was inadequate can include: disassociation of tissue structures, bubbles/holes in tissue sections, poor and irregular staining, shrunken cells, clumping of cytoplasm, condensation and less distinct nuclear chromatin, and autolysis/hemolysis of erythrocytes. Fixation with acetone is usually accomplished in minutes instead of hours because long exposure causes the tissue to become brittle and shrink. In contrast to fixation by formalin, ketones and alcohols are believed to fix tissue by physically stabilizing proteins by coagulation or precipitation without chemically reacting with them (e.g., aldehyde-mediated cross linking reactive groups).

Dehydration removes water from the tissue specimen to promote hardening. Replacement of water in the tissue specimen with a dehydrating agent also facilitates subsequent replacement of the dehydrating agent with material used for impregnation. This solvent/solute exchange is enhanced by using a volatile solvent for dehydration. Failure to dehydrate the specimen can lead to inadequate impregnation, poor ribbon formation during sectioning, clefts in tissue sections where water was not removed, dissociation of structures, water crystals in tissue sections, and poor staining.

Optionally, fat is removed from the tissue specimen with a solvent because fat impairs clearing and impregnation. Inadequate fat removal can result in spreading artifacts of tissue sections, wrinkling of tissue sections, and poor staining. Also optional is clearing the tissue specimen. The clearant extracts solvents used for dehydrating and/or defatting from the tissue specimen if they are not miscible with the impregnating agent. The tissue may become "clear" and its opacity may be reduced by the extraction.

Finally, once the tissue specimen is suitably fixed and dehydrated, it is hardened by impregnation with and/or embedded in an agent such as nitrocellulose, plastic, resin, or wax. Appropriate hardening of the tissue specimen with adequate preservation of morphology is required prior to placing the impregnated specimen in a block and obtaining ten micron or thinner sections with a microtome knife. Preferred impregnation materials are commercial wax formulae, mixtures of waxes of different melting points (e.g., liquid mineral oil and solid paraffin), and PARAPLAST medium. Paraffin has been chosen for use in the examples herein because it is inexpensive, easy to handle, and ribbon sectioning is facilitated by the coherence of structures provided by this material.

Following impregnation, the tissue specimen can be embedded to produce a block. The agent used to embed the tissue specimen is preferably the same as the material used for impregnation, but a different impregnating agent may also be used. The blocked tissue specimen can be mounted on a microtome to produce sections of between 0.5 µm and 50 µm, preferably between 2 µm and 10 µm. The tissue sections may be further processed for histochemical staining, antibody binding, in situ nucleic acid hybridization, amplification, or a combination thereof. The tissue specimens may be examined by microscopy, but other techniques for examining cellular properties may be used (e.g., automated flow or scanning cytometry, biopolymer detection or sequence determination, autoradiography, electrophoresis of protein or nucleic acid).

For wax-impregnated sections on glass slides made by the present invention, the wax may be melted and removed prior to staining or immunohistochemistry. The tissue section is rehydrated and then analyzed as described below with stains or antibodies. After staining is completed or the histochemical reaction is developed, the slide may be coverslipped and viewed under a microscope. Alternatively, the stained or antibody-decorated specimen may be studied with an instrument for cytometry. The tissue blocks may be stored for later examination.

Cellular and Molecular Analyses

Hematoxylin-eosin staining is commonly used for cytology and histology, and it may be used by pathologists as a standard for comparison. But other dyes and stains may be used. Enzymes endogenous to the tissue, or used as labels for antibodies and other affinity binders, may be localized in situ by an appropriate choice of substrate. The enzyme and substrate react to form a detectable product.

Antibody-antigen and ligand-receptor binding is the basis for sequence-specific detection of proteins. Proteins may be separated and isolated to at least partial purity by chromatography or electrophoresis. They may be detected by specific binding to an array, Western blotting, immunoprecitation (IP), enzyme-linked immunosorbent assay (ELISA), radioimmunoassay (RIA), and immunohistochemistry (IHC).

Tissue sections preserved by the present process may be subjected to immunohistochemistry. Antigen is preserved by the present invention and appropriately chosen tissue processing conditions. Nonspecific binding sites are blocked, antigen is bound by specific antibody (i.e., the primary antibody), and nonbound antibody is removed. If labeled with a probe or signal generating moiety, the primary antibody may be detected directly but it is preferred to attach the probe to a protein (e.g., a secondary antibody) that specifically binds the primary antibody. Secondary antibody may be raised against the heavy or light chain constant region of the primary antibody. This amplifies the signal generated by an antigen-antibody conjugate because each primary antibody will bind many secondary antibodies. Alternatively, amplification may occur through other specific interactions such as biotin-streptavidin. Antibody binding is performed in a small volume to reduce usage of expensive reagents and maintain a high binding rate; evaporation of this small volume is reduced by incubation in a humidity chamber. The signal generating moiety is preferably an enzyme which is not otherwise present in the tissue: for example, alkaline phosphatase and horseradish peroxidase may be attached to the secondary antibody or conjugated to streptavidin. Substrates are available for these enzymes that generate a chromogenic, fluorescent, or luminescent product that can be detected visually.

The staining pattern for antigen may be used to localize expression of antigen in the context of cellular structures revealed by counterstaining. Antigen expression can be use to identify cell or tissue type, developmental stage, tumor prognostic markers, degenerative metabolic processes, or infection by a pathogen.

Antigen-antibody binding may also be visualized with radioactive, fluorescence, or colloidal metal probes by autoradiography, epifluorescent microscopy, or electron microscopy, respectively. Alternatively, antigen may be extracted from tissue sections and directly detected or examined. For example, instead of immunohistochemistry, the antigen may be extracted, separated on a native or denaturing polyacrylamide gel, and detected by Western blotting.

Similar probes may be used to detect nucleic acid in the tissue section by in situ hybridization to identify genetic mutations or transcripts. Alternatively, the nucleic acid (e.g., DNA or RNA) may be extracted from tissue sections and directly detected or otherwise examined, or amplified prior to further genetic analysis.

The present invention is compatible with preparation of nucleic acids (e.g., DNA or RNA) from tissue before or after processing. See Ausubel et al. (*Current Protocols in Molecular Biology*, New York, N.Y.: Greene, 2002) and Sambrook & Russell (*Molecular Cloning*, 3rd Ed., Woodbury, N.Y.: CSHL, 2001) for molecular biology techniques.

The compositions and procedures of the present invention preserve material for genetic analysis and allows room temperature preservation and/or storage of tissue. Thus, genetic study is possible for tissues collected routinely in the pathology laboratory. Cytological observations may be correlated with genetic information by analyzing sorted cells by staining or antibody binding, and preparing nucleic acids from them for genetic analysis. Similarly, histological observations may be correlated with genetic information by analyzing one section by staining or antibody binding, and preparing nucleic acids from an adjacent section for genetic analysis. Anatomic details may be seen by reconstruction of serial sections. For example, diseased and normal regions of the same section may be compared to detect genetic differences (e.g., mutations, levels of transcription), disease history or progression may be characterized by comparing genetic differences in samples taken at several time points, and tumor evolution may be assessed by following the accumulation of genetic differences from primary cancer to metastasis.

Mutations may be germline and used to trace genetic predisposition of disease, or mutations may be somatic and used to determine genetic alterations in disease pathogenesis. The disease may be a metabolic or neurologic disorder, malignancy, developmental defect, or caused by an infectious agent.

For genetic analysis, formaldehyde-induced DNA abnormalities are eliminated and extraction of nucleic acid from archival material is enhanced. The study of RNA from preserved and/or stored tissue opens many previously unavailable avenues for diagnostic and research applications. Conventional RNA preservatives which inhibit or inactivate ribonucleases (e.g., ammonium chloride or sulfate, β-mercaptoethanol, diethyl pyrocarbonate, guanidine thiocyanate, placental ribonuclease inhibitor, urea) are not required to preserve fresh tissue in accordance with the present invention, but they may be used during extraction and isolation of RNA from preserved tissue. N-lauryl sarcosine and/or other detergents (e.g., TRITON X-100) may be used to lyse cell membranes and dissociate ribonucleoprotein complexes. RNA is precipitated by lithium chloride, but loss of RNA smaller than 5.8S can be minimized by preferential high-salt precipitation with isopropanol. Commercial kits for extracting and isolating RNA are available (e.g., Ambion, BD Biosciences Clontech, Invitrogen, Promega, Stratagene). RNA isolation techniques are described by Chirgwin et al. (Biochemistry, 18:294–299, 1979); Chomczynski & Sacchi (Anal. Biochem., 162:156–159, 1987); and in U.S. Pat. Nos. 4,843,155, 5,010, 183, 5,234,809, and 5,346,994. Solid tissue may be frozen and ground to a powder with a mortar and pestle, homogenized in DOUNCE or POLYTRON equipment, vortexing, sonication, use of bead or freezer mills, or a combination thereof. Crude or only partially purified DNA or RNA preparations may be genetically analyzed.

RNA may be isolated and at least partially purified in solution or by binding to a solid substrate (e.g., clay, silica, filter membrane, paramagnetic bead, cellulose in suspension or as a sheet). For example, RNA can be separated from DNA, proteins, and other biomolecules by binding to oligo (dT), differential precipitation, electrophoresis, sedimentation through a cushion, buoyant flotation in a gradient, or the like. Inactivation of ribonucleases in solutions or other reagents with diethyl pyrocarbonate (DEPC) is recommended.

The amount of RNA extracted from tissue may be measured by UV absorbence (an extinction coefficient of 1 $OD_{280}$/cm is 40 µg/ml RNA) or stoichiometric dye binding. Contamination can be assessed by UV absorbence: the $OD_{260}/OD_{280}$ ratio should be between 1.8 to 2.0 for substantially pure RNA, although the source of the tissue may bias the ratio to be greater than two. The strong secondary structure of RNA makes it difficult to visualize migration on an ethidium bromide (EtBr)-stained agarose gel after non-denaturing electrophoresis: multiple bands or a smear may result from a single RNA species separated under native conditions. Therefore, agarose or polyacrylamide gel electrophoresis under denaturing conditions (e.g., aldehydes, formamide, urea) is preferred to assess the integrity of RNA. Total RNA from a eukaryote will migrate under denaturing conditions as sharp bands of 28S and 18S ribosomal RNA (rRNA) in a ratio of 2:1 and a smear of messenger RNA (mRNA) from about 6 Kb to about 0.5 Kb. The 28S rRNA band should be approximately twice as intense as the 18S rRNA band; the smear of mRNA should be more intense between 2.0 Kb and 1.5 Kb. Only the mRNA smear should be visualized for polyadenylated (polyA$^+$) RNA. Densitometry of the rRNA bands can quantitate the degree of degradation. Alternatively, the mRNA may be subjected to a reverse transcription-polymerase chain reaction (RT-PCR) with primers to amplify a ladder of differently-sized products. Larger products should be reduced before smaller products because longer RNA are expected to be degraded faster than shorter RNA.

RNA extracted from preserved tissue in accordance with the present invention may be manipulated by genetic engineering and/or assayed. For example, RNA may be amplified by known techniques (e.g., direct transcription by an RNA-dependent RNA polymerase, transcription of double-stranded DNA containing a promoter recognized by a DNA-dependent RNA polymerase, replication by an RNA-dependent replicase). The RNA may be reverse transcribed to cDNA: the cDNA may then be amplified by known techniques (e.g., polymerase chain reaction or PCR, ligation chain reaction or LCR, transcription mediated transcription or TMA, transcription or replication). If a double-stranded DNA corresponding to the RNA is produced, then either RNA or cRNA may be transcribed using promoters or primers at the ends of a DNA substrate. Capture of target nucleic acid on a solid substrate is possible before, during, or after hybridization to localize or concentrate the RNA, cRNA or corresponding DNA.

Stringent hybridization is the basis for sequence-specific identification of nucleic acids. DNA may be detected by Southern blotting; RNA may be detected by Northern blotting. In solution, DNA or RNA may be detected by nuclease protection. Nucleic acids may be separated and isolated to at least partial purity by chromatography or electrophoresis.

Multiplex analysis may be used to monitor expression of different genes at the same time in parallel. Such multiplex analysis may be performed using probes complementary to the target nucleic acid (e.g., RNA, cRNA or corresponding DNA, single- or double-stranded DNA) arranged on a substrate (e.g., bead, fiber, membrane, or chip). An array may be spotted with probe or the probe may be synthesized in situ on a planar substrate; the probe may also be attached to individual beads or fibers as an ordered library. Simultaneous solution methods such as real-time relative RT-PCR, multiprobe ribonuclease protection assay or multiprimer pair amplification associate each transcript with a different length of detected product which is resolved by separation on the basis of molecular weight. Gene expression profiling or sequence identification may be performed using array or serial analysis of gene expression (SAGE) technology.

Amino acid sequences might be determined by Edman degradation of proteins or matrix-assisted laser desorption-ionization time-of-flight (MALDI-TOF) mass spectrometry of peptides from preserved and/or stored tissue. Nucleotide sequences might be determined by Maxam- Gilbert, Sanger, or sequencing-by-hybridization (SBH) procedures performed on nucleic acids (or amplified products thereof) from preserved and/or stored tissue. But the aforementioned techniques can detect and/or identify antigens and nucleic acids without necessarily determining their sequences.

The following examples demonstrate the usefulness and substantiate the effectiveness of the invention. In comparative examples, the advantages of the invention in comparison to the prior art are shown. These examples are intended to be merely illustrative of the invention, and are not intended to restrict or otherwise limit its practice.

EXAMPLES

Examples 1

DNA Extraction

DNA was extracted from tissue sections after preservation in different solutions (e.g., 10% polyethylene glycol 300 and 90% methanol) using an AquaPure Genomic DNA Isolation kit (Bio-Rad Laboratories) as follows:

Twenty mg of freshly minced mouse liver tissue or the same tissue preserved in 10% PEG/90% methanol was placed in a 1.5 ml microfuge tube containing 300 µl lysis solution. 1.5 µl of Proteinase K solution (20 mg/ml) was added to the lysate and mixed by inverting following by overnight incubation at 55° C. To the lysate, 1.5 µl of RNAse A solution (4 mg/ml) was added, mixed gently and incubated at 37° C. for 60 min. Samples were cooled to room temperature and 100 µl of protein precipitation solution was added. Samples were vortexed for 20 sec and then centrifuged at 16000 g for 3 min. Supernatant containing DNA was transferred to a fresh tube and precipitated with 300 µl of 100% isopropanol. Samples were mixed and centrifuged at 16000 g for one min. The DNA pellet was washed using 70% ethanol followed by air drying for 15 min. DNA was dissolved in 100 µl of DNA hydration solution and concentration was determined by UV spectrophotometry.

Ten mg of DNA was digested using TaqI EcoRI, or BamHI restriction enzyme. Five units of enzyme was used per microgram of DNA in overnight digestion using appropriate restriction enzyme buffer in total volume of 200 µl. Twenty µl was run on 0.8% agarose gel to determine whether DNA was digested.

DNA Results:
1. Preserved tissue provided a similar quantity of DNA as fresh tissue.
2. When tissue was preserved in formalin, about 30% less DNA was extracted as compared to extraction of fresh tissue or tissue preserved in 10% PEG/90% methanol.
3. Genomic DNA extracted from tissue preserved in 10% PEG/90% methanol could be digested with common restriction enzymes and was comparable in quality to DNA from fresh or formalin-fixed tissue.

Example 2

RNA Extraction

RNA was extracted from tissue sections after preservation in different solutions (e.g., 10% polyethylene glycol 300 and 90% methanol) using a Trizol RNA Isolation kit (Gibco BRL) as follows:

Fifty mg of fresh tissue or the same tissue preserved in 10% PEG/90% methanol was placed in about one ml of Trizol reagent and disrupted using a Polytron homogenizer. Samples were incubated at room temperature for 5 min and 0.2 ml of chloroform was added followed by hand mixing for 15 sec. Samples were centrifuged at 12000 g for 15 min at 5° C. Aqueous phase was removed and precipitated using 0.5 ml of isopropyl alcohol. Following 10 min incubation at room temperature, samples were cooled to 5° C. and centrifuged at 12000 g for 10 min. The RNA pellet was washed in 70% ethanol, air dried for 15 min, and dissolved in 100 µl of ribonuclease-free $H_2O$. The amount of RNA extracted was determined by UV spectrophotometry. Its quality was assessed by separating the RNA on a denaturing agarose gel and comparing the intensities of 28S and 18S ribosomal RNA bands.

Example 3

Detection of Antigen in Tissue Sections

As taught in U.S. Pat. No. 6,207,408, immunohistochemistry can be performed on tissue sections after fresh tissues were processed. In comparison, immunohistochemistry performed after preservation in different solutions (e.g., 10% polyethylene glycol 300 and 90% methanol) and then processed in accordance with U.S. Pat. No. 6,207,408. Results were compared to preserved tissue processed by conventional methods.

Uterine leiomyoma, malignant melanoma, pyelonephritis of kidney, and normal liver were studied. The following antibodies were used: epithelial markers (e.g., wide-spectrum cytokeratin, cytokeratin 7, epithelial membrane antigen); melanocyte markers (e.g., S100 protein, Melan A, tyrosinase, HMB-45); nuclear antigens (e.g., estrogen and progesterone receptors, Ki-67); leukocyte antigens (e.g., CD45, CD68, CD31); muscle markers (e.g., desmin, cladesmon, muscle actin); endothelial markers (e.g., Factor VIII related antigen, CD31); and hepatocellular and renal cell antigens. For all tissues, the immunohistochemical results were similar to those fixed in formalin except for weaker reactivity with antibody against hepatocellular antigen.

Immunohistochemical Procedure (steps 12 to 18 were carried out in a Dako Autostainer instrument):
1. Paraffin sections were cut to 3 microns.
2. Paraffin was melted by placing slides in a 58° C. oven (or preferably in a 37° C. oven) for 30 min.
3. Slides were dewaxed in xylene for 10 min.
4. Slides were rehydrated in a decreasing series of ethanol solutions (i.e., two baths of absolute, two baths of 95%, and one bath of 90%) for one min each.
5. Endogenous peroxidase was blocked with a solution of 6% hydrogen peroxide ($H_2O_2$) for 10 min.
6. Slides were rinsed by submerging in tap water for one min.
7. Racks of slides were placed in PBS bath submerged for one min.
8. Prepare target retrieval (TR) by adding 20 ml target retrieval (DAKO S1699) plus 180 ml $dH_2O$ in a green staining dish. Add $dH_2O$ to steamer and turn on steam. Place staining dish containing target retrieval solution inside steamer and let it heat for 30 min. TR solution should heat to 90° C.
9. Take out staining dish from steamer and place slides inside dish (use gloves) and steam for 20 min.
10. After steaming, let slides cool down in same container for 30 min.

11. Slides were placed in PBS buffer at room temperature (alternatively, slides may be stored in the buffer for 2 min to 18 hr and then staining continued).
12. Tissue sections were incubated with (a) Avidin Solution (DAKO X0590) for 10 min. The Avidin Solution was then rinsed off and tissue sections were incubated with (b) Biotin Solution (DAKO X0590) for 10 min. The Biotin Solution should be washed off before application of the first step of the staining procedure.
13. Specific primary antibody was added to each slide and then incubated for 30 min in a humidity chamber.
14. Slides were returned to the rack and the rack was submerged in a PBS bath for 2 min. Excess PBS was dried off each slide. Linking solution (DAKO LSAB+Kit, biotinylated anti-mouse, anti-rabbit and anti-goat) was added and incubated for 25 min in a humidity chamber.
15. Slides were returned to the rack and the rack was submerged in a PBS bath for 2 min.
16. Excess PBS was dried off each slide. Streptavidin-peroxidase-conjugate was added and incubated for 25 min in a humidity chamber.
17. Rack was submerged in PBS bath for 2 min and slides were then reacted with DAB chromogen (DAKO K3468). The slides were rinsed in fresh PBS for 4 min.
18. Slides were dried and counterstained with hematoxylin. NOTE: For nuclear antigens, dry excess PBS from slides and apply 1% cupric sulfate for 5 min. Slides were rinsed in tap water for 2 min and then placed in 0.2% fast green for one or a couple of seconds.
19. Slides were dehydrated through a series of alcohol solutions and then cleaned in xylene and coverslip.

Example 4

Comparison of Different Chemical Compositions

A preferred composition is a nonaqueous solution with 10% polyethylene glycol 300 (PEG) and 90% methanol. Given the need for a preservative composition that is amenable to both morphological and genetic analysis because morphology and RNA are preserved in the same tissue specimen, a variety of solutions were assessed for their ability to preserve at ambient temperature both characteristics of fresh, solid tissue and their compatibility with tissue processing in accordance with U.S. Pat. No. 6,207,408 and conventional methods.

RNA was degraded completely after the fresh tissue has been in contact for 15 min with either formalin (i.e., 10% formaldehyde in an aqueous buffer), gluteraldehyde, or methacam (i.e., 60% methanol, 30% chloroform, and 10% acetic acid). After fixation of fresh tissue in isopropanol (45%, 55% or 100%) for one hour, RNA was partially degraded. Fresh tissue fixed for 24 hr in either acetone or ethanol contained RNA, but produced inconsistent results. On the other hand, RNA was protected against degradation for up to three weeks at ambient temperature if fresh tissue has been in contact with either PEG or methanol.

The morphology of fresh tissue preserved in 10% PEG and 90% methanol was of the same quality as formalin-fixed tissue. Similarly, immunohistochemistry performed on fresh tissue preserved in 10% PEG and 90% methanol was of the same quality as formalin-fixed tissue. Morphology was maintained for at least seven days at room temperature. RNA was protected at ambient temperature for up to three weeks; RNA was protected at 4° C. for at least three weeks; RNA was protected at 37° C. for at least three days.

TABLE 1

Preservation of RNA at Room Temperature (about 25° C.)

| Preservation Time | | 15 min | 1 hr | 4 hr | 8 hr | 24 hr | 40 hr | 1 wk | 4 wk | 3 wk |
|---|---|---|---|---|---|---|---|---|---|---|
| 1 | PEG | ++ | ++ | ++ | ++ | ++ | ++ | ++ | ++ | ++ |
| 2 | Methanol | ++ | ++ | ++ | ++ | ++ | ++ | ++ | ++ | ++ |
| 3 | Ethanol* | ++ | ++ | ++ | ++ | ++ | ++ | ++ | ++ | ++ |
| 4 | Acetone* | ++ | ++ | ++ | ++ | ++ | ++ | ++ | ++ | ++ |
| 5 | Xylene | ++ | + | 0 | 0 | 0 | 0 | 0 | 0 | 0 |
| 6 | Isopropanol | ++ | + | + | + | + | + | + | + | + |
| 7 | 55% isopropanol | ++ | 0 | 0 | 0 | 0 | 0 | 0 | 0 | 0 |
| 8 | 40% isopropanol | ++ | 0 | 0 | 0 | 0 | 0 | 0 | 0 | 0 |
| 9 | 10% formalin | 0 | 0 | 0 | 0 | 0 | 0 | 0 | 0 | 0 |
| 10 | Chloroform | + | 0 | 0 | 0 | 0 | 0 | 0 | 0 | 0 |
| 11 | Glutaraldehyde | 0 | 0 | 0 | 0 | 0 | 0 | 0 | 0 | 0 |
| 12 | Methacarn | 0 | 0 | 0 | 0 | 0 | 0 | 0 | 0 | 0 |

++ No degradation of 28S and 18S ribosomal RNA bands
+ Degradation of 28S and 18S ribosomal RNA bands and/or lower band intensity
0 No bands
*Inconsistent results, perhaps due to water content of tissue For preservation of a cell or tissue, the polyethylene glycol 300 (PEG) concentration is between about 10% to about 20% and the methanol (MeOH) concentration is between about 80% to about 90%. Here, tissue (e.g., kidney, liver, skin, uterus) was contacted with the solution at about 25° C. for one hr to seven days. Maintenance of morphology (HISTO) was assessed after conventional tissue processing (TissueTek programmed as shown in U.S. Pat. No. 6,207, 408) or tissue processing in accordance with U.S. Pat. No. 6,207,408; while protection of RNA (RNA) was assessed after tissue processing in accordance with U.S. Pat. No. 6,207,408. Tissue was manually processed to prevent contamination with ribonuclease or other degradative enzymes. Satisfactory histomorphology is indicated by (+) and suboptimal morphology (i.e., fragmentation of section, irregular dye staining, variability in immunohistochemistry) is indicated by (+/−). RNA quality is indicated by ++, + and 0 (see the legend of Table 1).

TABLE 2

Varying Concentrations of PEG and Methanol

| | | 1 hr | | 24 hr | | 72 hr | | 1 wk | |
|---|---|---|---|---|---|---|---|---|---|
| Preservation Time | | | | | | | | | |
| PEG | MeOH | RNA | HISTO | RNA | HISTO | RNA | HISTO | RNA | HISTO |
| A  0 | 100 | ++ | (+/−) | ++ | (+) | ++ | (+) | ++ | (+) |
| B 10 | 90 | ++ | (+) | ++ | (+) | ++ | (+) | ++ | (+) |
| C 20 | 80 | ++ | (+) | ++ | (+) | + | (+) | ++ | (+) |
| D 30 | 70 | ++ | (+) | + | (+) | 0 | (+) | 0 | (+) |
| E 40 | 60 | + | (+) | + | (+) | 0 | (+) | 0 | (+) |
| F 50 | 50 | + | (+/−) | + | (+) | 0 | (+) | 0 | (+) |

Figure 1B:
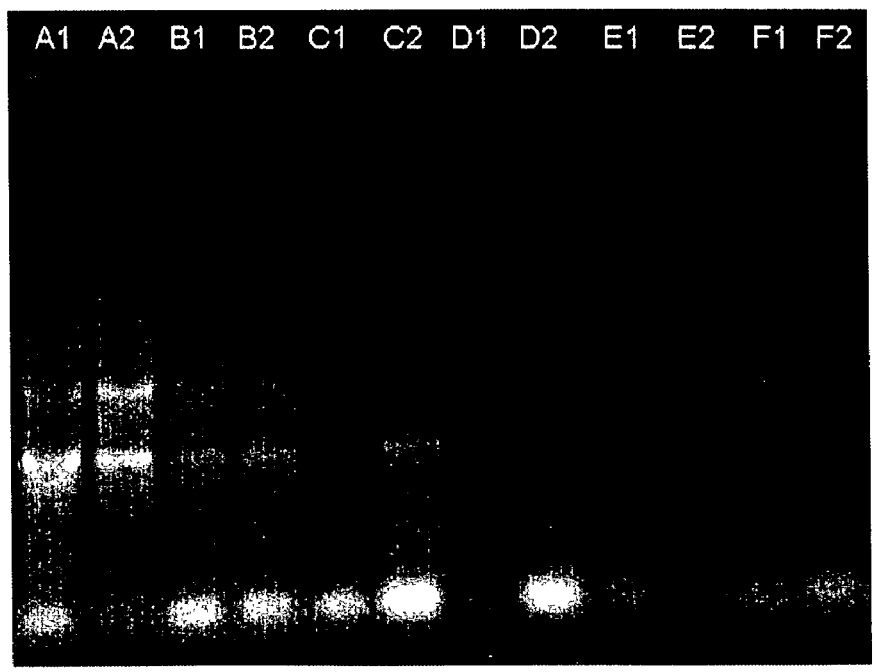
Figure 2A:
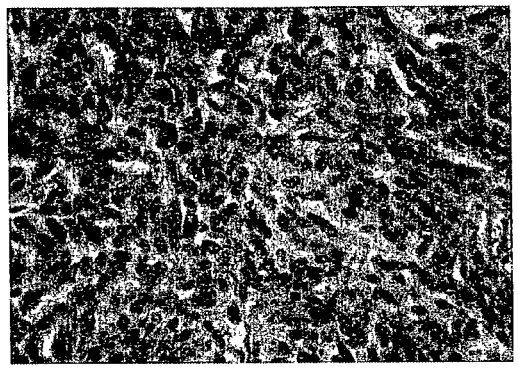
FIG. 2 shows hematoxylin-eosin stained tissue sections. Tissues were incubated in either 10% polyethylene glycol and 90% methanol (FIGS. 2A, 2C, 2E) or RNAlater (FIGS. 2B, 2D, 2F) for 48 hr (FIGS. 2A–2B), 72 hr (FIGS. 2C–2D), or one week (FIGS. 2E–2F) at about 25° C. They were processed either by the conventional method or in accordance with the method described in U.S. Pat. No. 6,207,408, and then stained. Magnification is 400× (FIGS. 2A–2F).
Figure 2B:
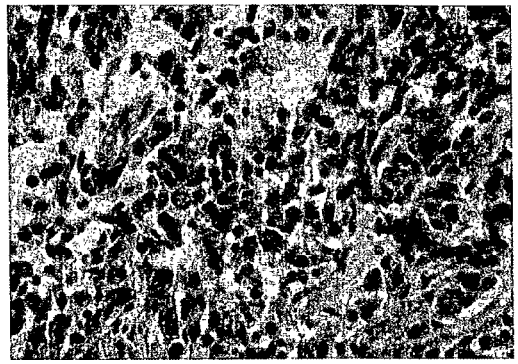
Figure 2C:
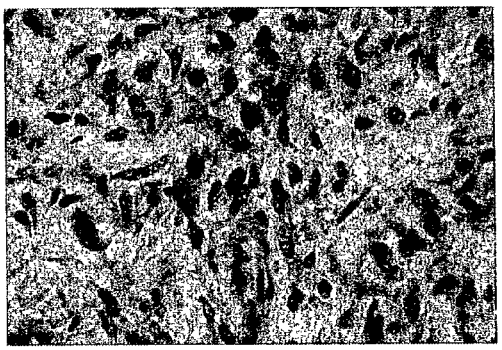
Figure 2D:
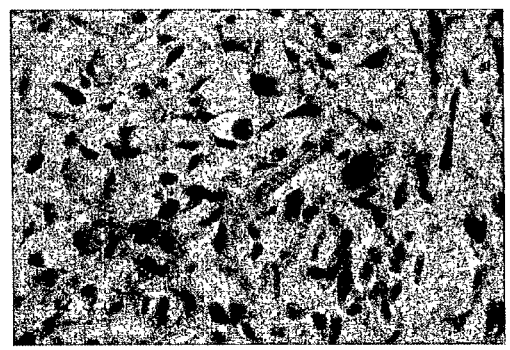
Figure 2E:
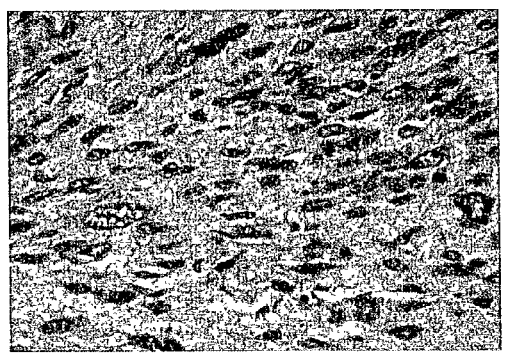
Figure 2F:
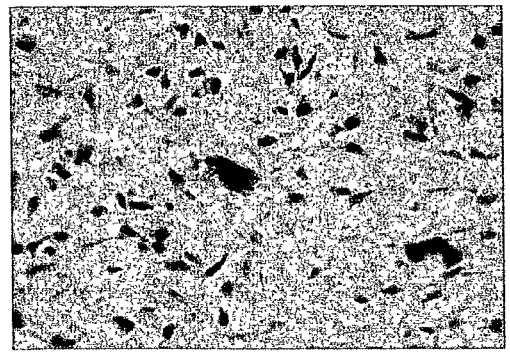

Both Table 2 and FIG. 1 show that 10% PEG and 90% methanol provides a composition that preserved both morphology and RNA. The ratio between 28S and 18S ribosomal RNA bands, as well as the smear of high molecular weight mRNA, confirmed the quality of the extracted RNA. A composition of methanol alone preserved RNA but hardening of tissue by contact with 100% methanol for a long time was an obstacle to histological analysis. At the other extreme, high concentrations of PEG preserved RNA but did not preserve morphology. Compositions of the invention, however, preserved both morphology and RNA content of tissues.

Preservation of tissue with compositions of the invention did not require reduced temperature. Preservation and storage was possible at ambient temperature (e.g., about 25° C.). Therefore, refrigeration or freezer facilities are not needed during transport or storage of tissue specimens.

Example 5

Comparison with RNAlater

RNAlater (Ambion) has been described by Florell et al. as preserving "both the integrity of tissue for pathologic diagnosis, and the RNA for molecular analyses" (Mod. Pathol., 14:116–128, 2001). Although the chemical composition of RNAlater is different from the invention, conventional tissue processing or tissue processing in accordance with U.S. Pat. No. 6,207,408 was used to determine if morphology was preserved.

Mouse liver was preserved in 10% PEG and 90% methanol or RNAlater for 48 hr, 72 hr, or one week. FIG. 2 shows that while morphology was preserved in tissue incubated in 10% PEG and 90% methanol, RNAlater did not preserve morphology at ambient temperature. After only 48 hr of incubation of tissue in RNAlater at about 25° C., there was disintegration of the nuclear membrane and condensation of the nuclear chromatin. There was progressive loss of morphological characteristics on prolonged incubation in RNAlater. But incubation of tissue in 10% PEG and 90% methanol at room temperature preserved morphological characteristics consistently for at least three weeks.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of the three transitions can be used to claim the invention.

It should be understood that an element described in this specification should not be construed as a limitation of the claimed invention unless it is explicitly recited in the claims. Thus, the claims are the basis for determining the scope of legal protection granted instead of a limitation from the specification which is read into the claims.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of the individual elements disclosed herein are considered to be aspects of the invention; similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A composition for preservation and/or storage of a cell or tissue, which is a nonaqueous solution comprising 5–20% polyethylene glycol (PEG) and 80–95% methanol.

2. The composition according to claim 1, wherein the nonaqueous solution comprises 10–15% polyethylene glycol (PEG) and 85–90% methanol.

3. The composition according to claim 1, wherein the nonaqueous solution comprises about 10% polyethylene glycol (PEG) and about 90% methanol.

4. The composition according to claim 1, wherein the nonaqueous solution consists essentially of about 10% polyethylene glycol (PEG) and about 90% methanol.

5. The composition according to claim 1, wherein the nonaqueous solution consists of about 10% polyethylene glycol (PEG) and about 90% methanol.

6. The composition according to claim 1, wherein the PEG has a molecular weight less than 600 daltons.

7. The composition according to claim 1, wherein the PEG has a molecular weight of 400 daltons or less.

8. A method of using the composition according to claim 1 comprising contacting at least a cell or tissue with the composition.

9. A method of making the composition according to claim 1 comprising mixing PEG and methanol.

10. A cell or tissue holder containing the composition according to claim 1 and adapted to hold at least a cell or tissue.

11. A method of preserving a cell or tissue comprising contacting at least a cell or tissue with the composition according to claim 1 within 30 minutes.

12. A method of storing cells or tissue comprising contacting at least partially preserved cells or tissue with the composition according to claim 1 for at least two weeks.

13. The method according to claim 11 further comprising extracting nucleic acid from at least a portion of the cell or tissue.

14. The method according to claim 13, wherein the nucleic acid is RNA.

15. The method according to claim 12 further comprising extracting nucleic acid from at least a portion of the cell or tissue.

16. The method according to claim 15, wherein the nucleic acid is RNA.

17. The method according to claim 13, wherein the nucleic acid is DNA.

18. The method according to claim 15, wherein the nucleic acid is DNA.

19. A method of protein detection and/or identification comprising:
 (a) contacting at least cells or tissue with a nonaqueous solution comprising 5–20% polyethylene glycol (PEG) and 80–95% methanol to preserve said cells or tissue,
 (b) extracting protein from preserved cells or tissue, and
 (c) detecting and/or identifying said protein.

20. A method of nucleic acid detection and/or identification comprising:
- (a) contacting at least cells or tissue with a nonaqueous solution comprising 5–20% polyethylene glycol (PEG) and 80–95% methanol to preserve said cells or tissue,
- (b) extracting nucleic acid from preserved cells or tissue, and
- (c) detecting and/or identifying said nucleic acid.

* * * * *